US006454768B1

(12) United States Patent
Jackson

(10) Patent No.: US 6,454,768 B1
(45) Date of Patent: *Sep. 24, 2002

(54) REMOVABLE GRIPPING SET SCREW

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

This patent is subject to a terminal disclaimer.

(21) Appl. No.: 09/729,846

(22) Filed: Dec. 5, 2000

(51) Int. Cl.$^7$ ................................. A61B 17/56
(52) U.S. Cl. ................ 606/61; 606/73; 411/5
(58) Field of Search ............... 606/61, 72, 73, 606/65, 69, 70, 71, 62; 411/1–5; 439/814

(56) References Cited

U.S. PATENT DOCUMENTS

| 791,548 | A | | 6/1905 | Fischer |
|---|---|---|---|---|
| 2,201,087 | A | | 5/1940 | Hallowell |
| 2,239,352 | A | | 4/1941 | Cherry |
| 2,295,314 | A | | 9/1942 | Whitney |
| 2,532,815 | A | | 12/1950 | Kindsvatter |
| 2,553,337 | A | | 5/1951 | Shafer |
| 2,778,265 | A | | 1/1957 | Brown |
| 2,877,681 | A | | 3/1959 | Brown |
| 2,927,332 | A | | 3/1960 | Moore |
| 3,143,029 | A | | 8/1964 | Brown |
| D200,217 | S | | 2/1965 | Curtiss |
| 3,370,341 | A | | 2/1968 | Allsop |
| 3,498,174 | A | | 3/1970 | Schuster et al. |
| 3,584,667 | A | | 6/1971 | Reiland |
| 3,812,757 | A | | 5/1974 | Reiland |
| 3,963,322 | A | * | 6/1976 | Gryctko ............ 439/814 |
| 4,269,246 | A | | 5/1981 | Larson et al. |
| 4,492,500 | A | | 1/1985 | Ewing |
| 4,506,917 | A | | 3/1985 | Hansen Arne |
| 4,641,636 | A | | 2/1987 | Cotrel |
| 4,763,644 | A | | 8/1988 | Webb |
| 4,764,068 | A | | 8/1988 | Crispell |
| 4,790,297 | A | | 12/1988 | Luque |

(List continued on next page.)

FOREIGN PATENT DOCUMENTS

| DE | 3630863 | 3/1988 |
|---|---|---|
| DE | 3738409 | 5/1989 |
| EP | 195455 | 9/1986 |
| EP | 172130 | 2/1987 |
| EP | 276153 | 7/1988 |
| EP | 465158 | 1/1992 |
| FR | 2467312 | 4/1981 |
| GB | 203508 | 9/1923 |
| WO | PCT/CH91/00174 | 3/1992 |
| WO | PCT92/03100 | 3/1992 |
| WO | PCT94/10927 | 5/1994 |
| WO | PCT9410944 | 5/1994 |
| WO | PCT96/06576 | 3/1996 |

Primary Examiner—Pedro Philogene
(74) Attorney, Agent, or Firm—John C. McMahon

(57) ABSTRACT

A medical implant set screw having a base joined to a head by a breakaway region. The set screw has a longitudinally and axially extending bore that passes through the head and into the base. The bore has a stepdown within the base so as to produce a first circumferential edge. The base breaks away from the head at a predetermined torque during installation so as to expose an upper surface. The portion of the bore in the base intersecting with the upper surface forms a second edge that is spaced above the edge formed by the step and which has a somewhat greater diameter than the edge formed by the step. The two edges of the bore are sized, positioned and spaced so as to allow an easy-out to simultaneously engage both to improve gripping by the easy-out of the base during removal thereof. The set screw base also includes a threadform having a leading edge and a trailing edge that both intersect with a plane passing through an axis of rotation of the set screw so as to form intersections that both slope rearwardly from an inner edge to an outer edge thereof.

9 Claims, 2 Drawing Sheets

U.S. PATENT DOCUMENTS

| | | | |
|---|---|---|---|
| 4,815,453 A | | 3/1989 | Cotrel |
| 4,838,264 A | | 6/1989 | Bremer et al. |
| 5,005,562 A | | 4/1991 | Cotrel |
| 5,022,791 A | | 6/1991 | Isler |
| 5,067,955 A | | 11/1991 | Cotrel |
| 5,073,074 A | | 12/1991 | Corrigan et al. |
| 5,092,635 A | | 3/1992 | DeLange et al. |
| 5,129,388 A | | 7/1992 | Vignaud et al. |
| 5,147,360 A | | 9/1992 | Dubousset |
| 5,154,719 A | * | 10/1992 | Cotrel .......................... 606/73 |
| 5,261,907 A | | 11/1993 | Vignaud et al. |
| 5,261,912 A | | 11/1993 | Frigg |
| 5,282,707 A | | 2/1994 | Palm |
| 5,312,404 A | | 5/1994 | Asher et al. |
| 5,346,493 A | | 9/1994 | Stahurski et al. |
| 5,358,289 A | | 10/1994 | Banker et al. |
| 5,364,400 A | | 11/1994 | Rego, Jr. et al. |
| 5,382,248 A | | 1/1995 | Jacobson et al. |
| 5,385,583 A | | 1/1995 | Cotrel |
| 5,427,418 A | | 6/1995 | Watts |
| 5,487,742 A | | 1/1996 | Cotrel |
| 5,496,321 A | | 3/1996 | Puno et al. |
| 5,499,892 A | * | 3/1996 | Reed .............................. 411/5 |
| 5,507,747 A | | 4/1996 | Yuan et al. |
| 5,562,663 A | | 10/1996 | Wisnewski et al. |
| 5,602,553 A | | 2/1997 | Trebing et al. |
| 5,630,817 A | | 5/1997 | Rokegem et al. |
| 5,643,260 A | | 7/1997 | Doherty |
| 5,653,710 A | | 8/1997 | Harle |
| 5,697,929 A | * | 12/1997 | Mellinger .................... 606/61 |
| 5,741,254 A | | 4/1998 | Henry et al. |
| 5,928,236 A | * | 7/1999 | Augagneur et al. ........... 606/73 |
| 5,941,885 A | * | 8/1999 | Jackson |
| 5,980,523 A | * | 11/1999 | Jackson |
| 6,001,098 A | | 12/1999 | Metz-Stavenhagen et al. |
| 6,056,753 A | | 5/2000 | Jackson |
| 6,059,786 A | | 5/2000 | Jackson |
| 6,063,090 A | | 5/2000 | Schlapfer |
| 6,074,391 A | * | 6/2000 | Metz-stavenhagen et al. 606/61 |
| 6,077,262 A | | 6/2000 | Schlapfer et al. |
| 6,102,913 A | | 8/2000 | Jackson |

* cited by examiner

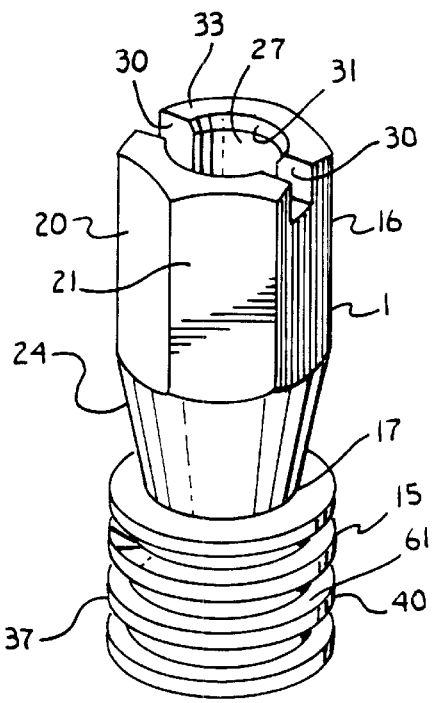
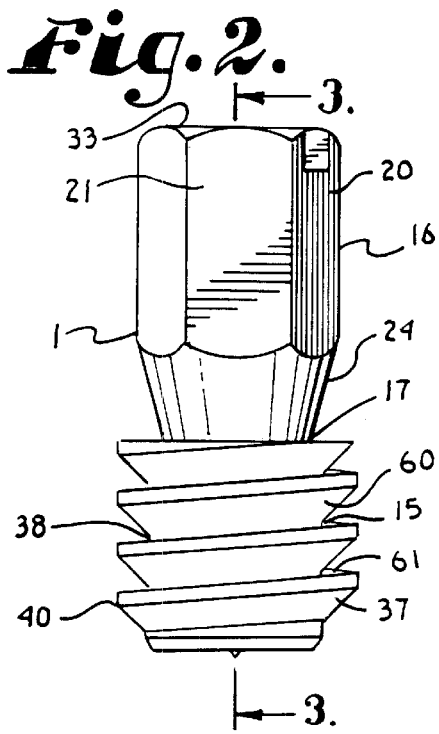
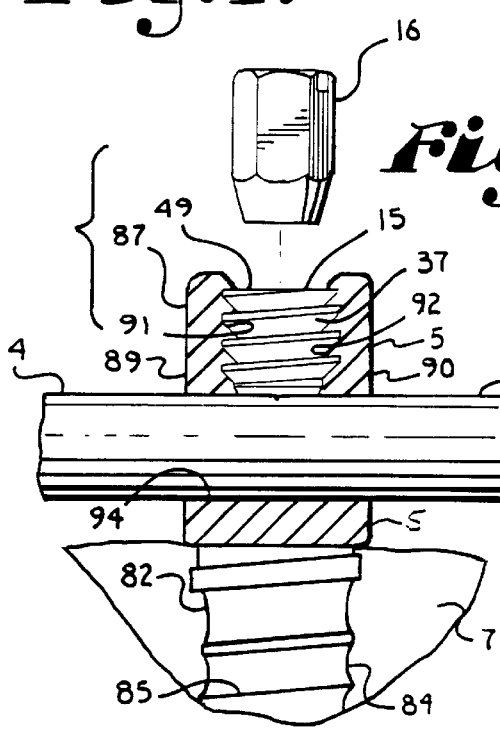
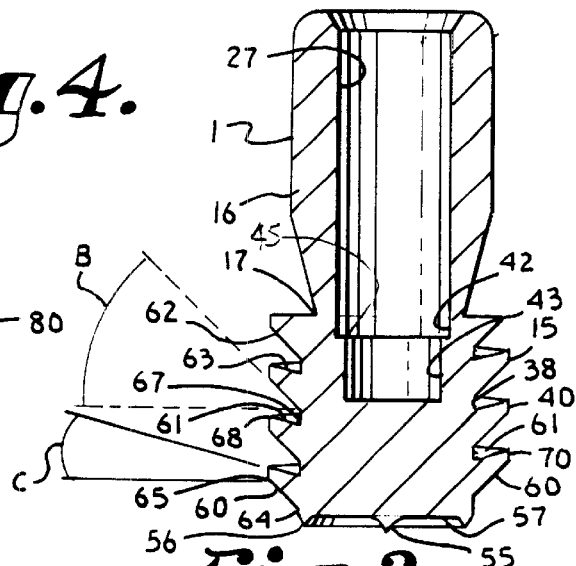

REMOVABLE GRIPPING SET SCREW

BACKGROUND OF THE INVENTION

The present invention is directed to a set screw, especially a set screw for use in medical implants, that includes a step-down internal bore for improved interface with an easy-out for purposes of removal and an external thread that draw walls of the structure within which the set screw is placed toward the set screw rather than urging the walls away from the set screw.

Set screws are used in many ways in order to lock one element of a device relative to another. Set screws are quite important in the art of medical implants, as it is often necessary to capture one element of the implant relative to another and to then lock the two relative to one another to prevent subsequent movement therebetween. Failure to properly lock two elements of a medical implant together may result in failure of the implant and possible serious injury to the patient within which the implant is placed.

With medical implants, it is desirable to have very light-weight and low profile elements so that the overall implant impacts as little as possible upon the patient. If set screws could be manufactured that were quite large and the other elements of the implants could be likewise quite large and such would still have a low profile, it would be much easier to construct a suitable set screw in such implants. However, large size and low profile are incompatible goals. Size, weight and profile must all be taken into consideration and minimized, as much as possible.

In order to provide sufficient strength and friction to resist movement of the various elements, once the set screw is seated, it is necessary to apply a fairly substantial torque to the set screw. While some set screws are torqued without a head, many of the set screws currently in use in medical implants have a driving head that breaks away from the remainder of the set screw at a preselected torque in order to assure that the set screw is sufficiently torqued to provide the necessary strength and locking friction. The head is also broken away in order to assure that the set screw is not over-torqued and the threads stripped. Further, the head is typically broken away in order to provide the low profile and light weight that is desired in such set screws.

Because the driving head is typically broken away and because it is sometimes necessary to remove the set screw after implantation and setting thereof, some mechanism must be provided in order to remove the set screw. Various structures have been provided for this purpose in prior art devices. The prior art structures have had varying degrees of success, but have typically been most effective in set screws having a diameter that is comparatively large, such as 8 to 10 millimeters, because such larger set screws provide greater surface and volume to allow the placement of removal structure of one kind or another on the set screw.

Easy-outs are a commonly used tool that have been utilized to remove bolts and screws that have been used in various mechanical devices and that have no other means for gripping. Such have especially been used for bolts where the heads have been broken away. However, the term "easy-out" is somewhat of a misnomer in that such are actually very difficult tools to utilize. This is especially true when dealing with set screws of the size used in medical implants which often range from 5 to 10 millimeters in diameter. It has been found that set screws of this size with a conventional axial bore are often not removable by an easy-out, because the easy-out has too little edge or surface upon which to grip. Further, the edge that has been previously provided is often torn away by use of the easy-out to a point where there becomes less and less edge to grip with each subsequent attempt. Consequently, it is desirable to produce a set screw having a head that breaks away from a base of the set screw at a preselected torque yet provides a highly gripable surface or edge on the set screw for use in conjunction with an easy-out design.

Another inherent problem in certain medical implants with set screws of a conventional type is that such set screws typically utilize threads which are referred to as V-threads. The edges of a cross-section of V-threads has a V shape. V-threads work reasonably well in devices where a bore is provided that completely surrounds the set screw and has a mating thread that mates with the thread of the set screw. However, many medical implants, such as open headed bone screws, do not provide for a bore that will entirely encircle the set screw. In such implants, the set screw also functions as a closure and spans between a pair of discontinuous threaded surfaces. When V-thread set screws are utilized for this purpose, the forces exerted by the set screw during torquing are partially parallel to the axis of rotation of the set screw and partially radially extending outwardly from the set screw. The radial outward forces can and frequently do spread the arms of the head within which the set screw is being torqued sufficiently to allow for failure of the set screw. Buttress-type threads have been utilized for the purpose of trying to reduce the radial outward forces that are exerted by the threads. In buttress-type thread screws, the trailing surface of the thread normally has a cross-section edge that is parallel to or is fairly close to being parallel to a radius of the set screw. Sometimes such surfaces are referred to as flat, but normally the cross section has a slight inclination of from 5 to 10 degrees so that a smaller, but yet substantial force, is exerted radially outward by the buttress thread screws as compared to the V-shaped thread screws. Consequently, it is desirable to also have a set screw of this type wherein the threads are designed to exert an inwardly directed force to pull opposing walls of an implant toward the set screw, rather than urge the walls away from the set screw.

SUMMARY OF THE INVENTION

A set screw having a threaded base and a driving head that is breakable from the base at a preselected torque at a breakaway region. A bore extends axially through the head and into the base. The bore has a first larger diameter through the head and a portion of the base and a second smaller diameter through a portion of the base providing a stepdown transition between the bores. The stepdown has an internal circumferential edge which cooperates with an edge of the larger diameter portion of the bore when the head is broken from the base, so as to provide two edges in spaced relationship to one another. In particular, the two circumferential edges are sized, spaced and positioned so as to mate with the face of an easy-out positioned therein. The angle formed by joining points on the edges together that are associated with a plane passing through an axis of rotation of the screw and the edges, is the same as the angle formed by an engaging face of the easy-out and an axis of rotation of the easy-out. In this manner the easy-out with a reverse threaded surface is able to simultaneously cut into and engage both of the edges. The force that is able to be exerted on the set screw through the easy-out is highly proportional to the length of the edges and/or surface that the easy-out can engage. Consequently, the two edges are designed and positioned to mate with the conical surface of an easy-out to allow for the best gripping of the easy-out relative to the base.

The base also includes an external helically wound thread. The thread has a leading surface and a trailing surface relative to advancement of the set screw when rotated about a central axis clockwise. A cross-section of the set screw in a plane passing through the axis of rotation forms intersections with the leading and trailing edges that both slope rearwardly from an inner edge to outer edge thereof.

OBJECTS AND ADVANTAGES OF THE INVENTION

Therefore, the objects of the present invention are to provide a set screw having a base and a head that breaks away from the base at a breakaway region, so as to provide a low profile subsequent to setting of the set screw; to provide such a set screw having an axially extending bore that passes through the head and has a stepdown region in the base wherein the bore passes from a region of a larger diameter to a region of a smaller diameter; to provide such a set screw wherein the breakaway of the head from the base produces a circumferential ring at the mouth of the bore; to provide such a set screw wherein the edge at the mouth of the bore and the edge at the stepdown region of the bore are sized, shaped and spaced so as to mate with a reverse threaded conical surface of an easy-out, so as to improve the engagement and gripping of the easy-out relative to the set screw base; to provide such a set screw having two or more step-down edges to improve gripping by an easy out; to provide such a set screw wherein the base has an external thread that has both a leading edge and a trailing edge that slope rearwardly with respect to clockwise advancement of the set screw in a bore from an inner diameter of the thread to an outer diameter thereof; to provide such a set screw that exerts both axial reactive forces and inward radial reactive forces on an implant bore within which the set screw is placed; to provide such a set screw that is highly effective at setting one element of an implant relative to another element of the implant, but is readily removed should removal be necessary; and to provide such a set screw which is easy to use and especially well adapted for the intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a set screw in accordance with the present invention.

FIG. 2 is a side elevational view of the set screw.

FIG. 3 is a cross-sectional view of the set screw, taken along line 3—3 of FIG. 2.

FIG. 4 is a side elevational view of the set screw illustrated securing together a first implant and a second implant, with the head of the set screw having just broken away from a base thereof and with portions of the second implant broken away to show internal detail thereof.

DETAILED DESCRIPTION OF THE INVENTION

Figure 5:
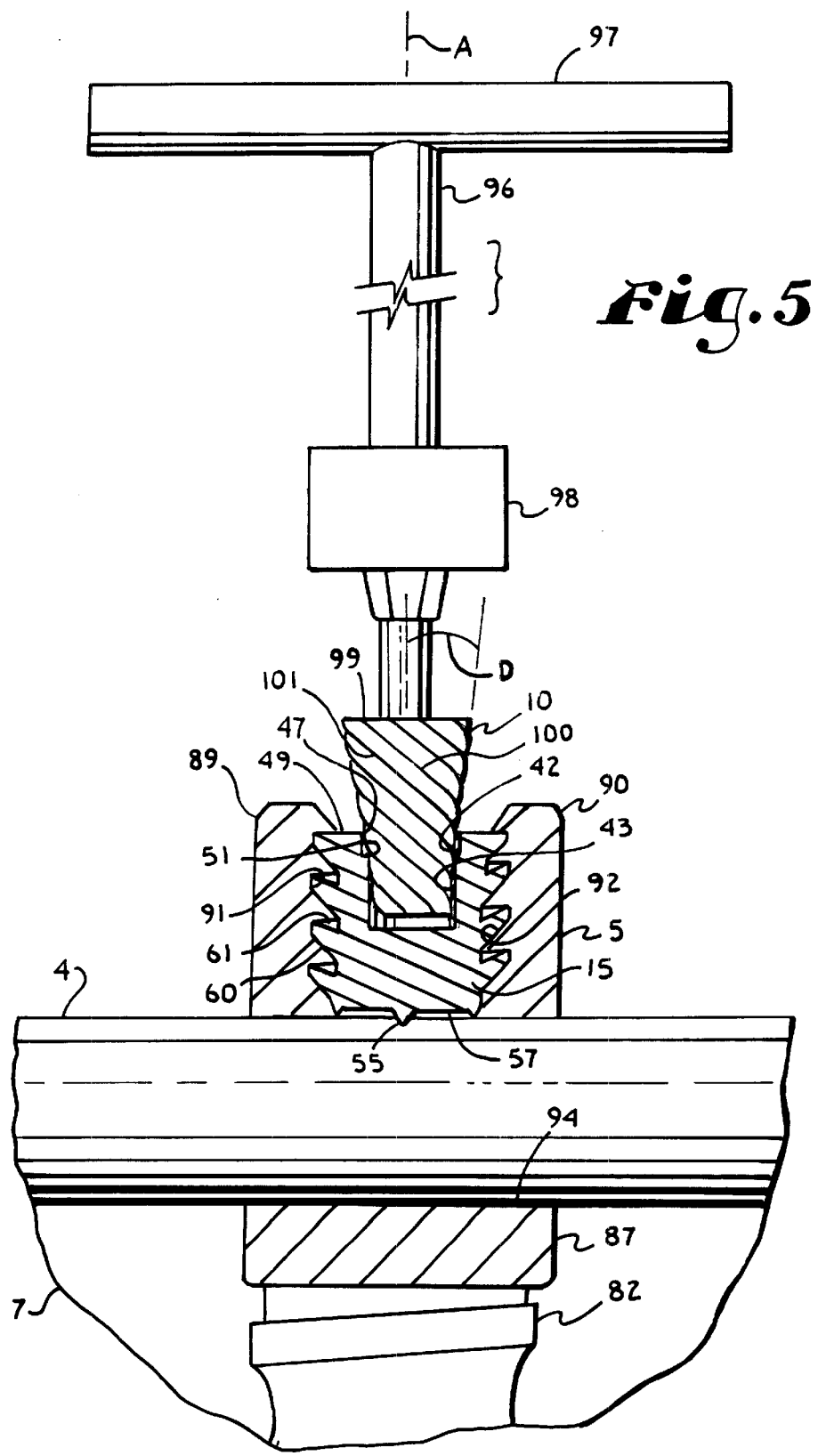
FIG. 5 is a side elevational view of the set screw, first implant and second implant on an enlarged basis, illustrating the set screw being removed by utilization of an easy-out and with portions of the set screw and second implant broken away to show internal detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a set screw in accordance with the present invention. The set screw 1 is utilized in conjunction with a first medical implant 4 and a second medical implant 5 which in turn is fixed in a vertebral body 7 of a patient's spine. The set screw 1 is also used in conjunction with an easy-out 10.

The set screw 1 includes a base 15 and a driving head 16 that are joined by a breakaway region 17. The set screw 1 has an axis of rotation generally indicated by the reference letter A. The head 16 has an upper outer surface 20 that is composed of six faces 21 that are equally spaced from the axis of rotation A and which are joined in a polyhedral shape having a hexagonal cross-section. The outer surface 20 is sized and shaped to receive a socket tool (not shown) of a conventional type for driving screws and bolts. A lower portion 24 of the head 16 joins the outer surface 20 with the base 15 and has a generally truncated conical shape. The breakaway region 17 is located whereat the lower conical portion 24 of the head 16 is of least diameter and cross-section. The head 16 also has an internal bore 27 that is coaxially aligned with the axis of rotation A and which extends completely through the head 16. As can be seen in FIG. 3, the head 16 has the least cross-section in a horizontal plane at the breakaway region 17 due to the presence of both the vertical convergence of the lower conical portion 24 and the location of the bore 27.

A pair of opposed slots 30 are also located in the top of the head for mating with a tool and an internal surface 31 of the head where the bore 27 opens onto an upper surface 33 is chamfered.

The base has a generally cylindrical shaped body 37 with a radial outer surface 38 having a thread 40 helically wound about the surface 38. When the base 15 is unbroken from and still integral with the head 16, the head bore 27 extends into the base 15 forming a base upper bore or bore portion 42. The base 15 has a coaxial lower bore or bore portion 43. The bore 42 is of larger diameter than the lower bore 43 and there is a shoulder 45 therebetween. At the upper end of the lower bore 43 and inner side of the shoulder 45 is a circumferential edge 51.

When the base 15 breaks from the head 16, a planar upper surface 49 intersecting with the bore portion 42 is exposed. An inner edge 47 is located at the intersection of the bore portion 42 and upper surface 49. The lower edge 51 is thus of a smaller diameter than the upper edge 47 and spaced coaxially therebelow.

The base 15 also has a lower coaxially aligned point 55 and a circumferential cutting ring 56 located on a bottom 57 thereof.

The thread 40 can be seen in cross-section in FIG. 3 and has a leading surface 60 and a trailing surface 61 relative to clockwise advancement of the set screw 1 by rotation about the axis A in a mating thread, as will be described later.

Intersections 62 and 63 of the leading surface 60 and trailing surface 61 respectively with a plane passing through the axis of rotation A both slope rearwardly, again with respect to advancement of the set screw during installation. In particular, the leading surface 60 has an inner edge 64 and an outer edge 65 and the trailing surface 61 has an inner edge 67 and an outer edge 68. The leading surface 60 slopes rearwardly from the inner edge 64 to the outer edge 65 and the trailing surface 61 slopes rearwardly from the inner edge 67 to the outer edge 68 thereof. Preferably, the inner edges 64 and 67 are more greatly spaced than the outer edges 65 and 68 so that the thread 40 has a generally triangular configuration in cross-section with an outer tip removal. An outer vertical wall 71 joins the leading surface 60 to the trailing surface 61.

With respect to a radius of the set screw, an angle B between such a radius and the intersection 62 of the leading surface 60 with a plane passing through the axis A is preferably within a range from 3 to 40 degrees and most preferably within a range from 7 to 10 degrees. Also preferably the angle C between an intersection 63 of the trailing surface 61 with the radius of the set screw 1 is preferably within a range of from 30 to 60 degrees and most preferably within a range of from 40 to 50 degrees.

The first implant 4 of the illustrated embodiment is an elongate rod having a cylindrical surface 80. The second implant 5 is a bone screw 82 having a shank 84 with an external thread 85 that is screwed into the vertebral body 7, such as is shown in FIGS. 4 and 5. The bone screw 82 also has a head 87 with a pair of upstanding arms 89 and 90. Each of the arms 89 and 90 has an internal threaded surface 91 and 92 respectively that are threaded to matingly receive the thread 40 of the set screw 1, as is shown in FIG. 4. The cylindrical surface 80 of the first implant 4 is received in a channel 94 of the head 87 which is, in the present embodiment, closed by the set screw 1.

The easy-out 10 has a handle 96 with a cross member 97 for turning. Opposite the cross member 97 is a chuck 98 joined with a head 99. The head 99 has an outer surface 100 that is in the shape of a truncated cone and which has a reverse thread 101 helically wound thereabout. The angle of an intersection of the head 99 with a plane passing through the axis of the head 99 is represented by the angle D and is the same angle as is formed by joining points of the edges 47 and 51 intersected by a plane passing through the axis A, as is seen in FIG. 5. In this manner the easy-out head outer surface 100 is mateable with or engages both of the edges 47 and 51 simultaneously.

In use the set screw 1 is inserted between the second implant arms 89 and 90 and threadably received with respect to the surfaces 91 and 92, so as to advance, that is rotate and move downwardly relative to the second implant 5 in FIG. 4. The first implant 4 is positioned in the channel 94 of the second implant 5 prior to installation of the screw 1 and, as the set screw 1 advances, it engages the first implant 4. Upon engagement with the first implant 4, additional torque is applied to the set screw 1 until a preselected torque is achieved at which time the head 16 breaks from the base 15, as is shown in FIG. 4. At this time the set screw base 15 is set with respect to locking the first implant 4 in position relative to the second implant 5. The thread 40 of the set screw base 15 exerts a combined axial and radial inward force against the second implant arms 89 and 90 so as to pull the arms 89 and 90 toward the set screw base 15.

If it is desired to remove the set screw base 15 once seated, the easy-out 10 is placed such that the easy-out head 99 is located within the bores 42 and 43 in such a manner that the head outer surface 100 engages both of the edges 47 and 51 simultaneously. The easy-out 10 is then rotated in a counterclockwise manner, while applying sufficient force that the thread 101 on the head outer surface 100 grips the set screw base 15 at the edges 47 and 51 so as to transfer torque thereto until the set screw 1 unscrews from the implant 5.

While the present illustrated embodiment shows only a single stepdown with the bores 42 and 43 of the base 15, it is foreseen that additional stepdowns could be utilized to further improve the engagement of the easy-out head 99 with edges of the base 15 and to thereby improve the efficacy of the easy-out 10 in removing a set screw base 15. It is also noted that the step-downs can be relatively close and the overall depth of the combined bores can be comparatively shallow, since total length of the shoulder edge available to the easy-out is more important than overall axial length of the bores or easy-out.

It is to be understood that while certain forms of the present invention have been illustrated and described herein, it is not to be limited to the specific forms or arrangement of parts described and shown.

What is claimed and desired to be secured by Letters Patent is as follows:

1. A set screw comprising:
    a) a body having an axis of rotation and a radially outer threaded surface, an upper surface and a lower surface;
    b) said body having a multi-diameter bore extending axially from said upper surface;
    c) said bore having a first diameter upper portion adjacent said upper surface and forming a first circumferential edge with said upper surface; said bore lower portion having a second diameter smaller than said first diameter and beginning at a shoulder spaced from said upper surface; said bore lower portion having a second circumferential edge at the inner side of said shoulder; and
    d) said first and second edges being sized and spaced so as to be adapted to simultaneously engage an outer surface of an easy out for purposes of removal.

2. The set screw according to claim 1 including:
    a) a head for gripping and driving during installation.

3. The set screw according to claim 2 wherein:
    a) said head is initially secured to said body by a breakaway region and said head separates from said bore upon the application of a preselected torque.

4. The set screw according to claim 3 wherein:
    a) said breakaway region is located at the position having the least cross-sectional area between said head and body in a plane perpendicular to an axis of rotation of said screw.

5. The set screw according to claim 4 wherein:
    a) said breakaway region and said first edge are both in a common plane perpendicular to said axis of rotation.

6. The set screw according to claim 1 wherein:
    a) said threaded outer surface has a helically wound threadform thereon; said set screw has a direction of normal advancement along said axis of rotation;
    b) said threadform has a leading surface and a trailing surface; and
    c) both said leading surface and said trailing surface slope rearwardly relative to said direction of advancement from inner edges to outer edges thereof.

7. The set screw according to claim 6 in combination with an open headed bone screw having a pair of spaced arms with facing threaded surfaces that mate with the thread on said set screw during use such that said set screw closes between said arms.

8. The set screw according to claim 1 in combination with a medical implant having a first element and a second element wherein said set screw is received in a threaded bore of said first element and has a bottom that abuts against said second element during use to lock the second element in fixed position relative to said first element.

9. In a set screw having a body with a threaded outer surface and an axially aligned bore; the improvement comprising:

a) said bore having an upper first edge and a stepdown shoulder with a second edge; said first and second edges being positioned and spaced to be adapted to both simultaneously engage an easy-out for removal.

* * * * *